United States Patent
Yang et al.

(10) Patent No.: US 9,202,296 B2
(45) Date of Patent: Dec. 1, 2015

(54) METAL ARTIFACTS REDUCTION FOR CONE BEAM CT

(75) Inventors: Dong Yang, Rochester, NY (US); Robert A. Senn, Pittsford, NY (US)

(73) Assignee: Caresteam Health, Inc., Rochester, NY (US)

( * ) Notice: Subject to any disclaimer, the term of this patent is extended or adjusted under 35 U.S.C. 154(b) by 289 days.

(21) Appl. No.: 13/234,472

(22) Filed: Sep. 16, 2011

(65) Prior Publication Data

US 2013/0070991 A1    Mar. 21, 2013

(51) Int. Cl.
G06K 9/00 (2006.01)
G06T 11/00 (2006.01)
G06F 3/00 (2006.01)
A61B 6/00 (2006.01)

(52) U.S. Cl.
CPC ............ G06T 11/008 (2013.01); A61B 6/5258 (2013.01); G06F 3/00 (2013.01); G06K 9/00221 (2013.01); G06K 9/00335 (2013.01); G06K 9/00389 (2013.01)

(58) Field of Classification Search
None
See application file for complete search history.

(56) References Cited

U.S. PATENT DOCUMENTS

| | | | |
|---|---|---|---|
| 5,270,926 A | 12/1993 | Tam | 378/4 |
| 5,999,587 A | 12/1999 | Ning et al. | 378/4 |
| 8,233,586 B1 * | 7/2012 | Boas | G06T 11/005 378/207 |
| 8,503,750 B2 * | 8/2013 | Benson | A61B 6/5258 378/4 |
| 2008/0112603 A1 * | 5/2008 | Boyden | G01R 33/565 382/131 |
| 2008/0199060 A1 * | 8/2008 | Boyden | G06T 5/006 382/131 |
| 2008/0253635 A1 * | 10/2008 | Spies | G06T 11/008 382/131 |
| 2009/0074278 A1 * | 3/2009 | Beaulieu | A61B 6/032 382/131 |
| 2009/0087065 A1 * | 4/2009 | DaSilva | A61B 6/037 382/131 |
| 2009/0171244 A1 | 7/2009 | Ning et al. | 600/567 |
| 2010/0054569 A1 * | 3/2010 | Bruder | A61B 6/032 382/131 |
| 2010/0183214 A1 * | 7/2010 | McCollough | A61B 6/032 382/131 |
| 2011/0007956 A1 * | 1/2011 | Meyer | A61B 6/032 382/131 |
| 2011/0013817 A1 | 1/2011 | Medow | 382/131 |
| 2011/0081071 A1 * | 4/2011 | Benson | A61B 6/5258 382/154 |

OTHER PUBLICATIONS

L.A. Feldkamp et al., "Practical cone-beam algorithm", 1984 Optical Society of America, vol. 1, No. 6, Jun. 1984, pp. 612-619.

* cited by examiner

Primary Examiner — Avinash Yentrapati (57) ABSTRACT

A method for suppressing metal artifacts in a radiographic image, the method executed at least in part on a computer, obtains at least one two-dimensional radiographic image of a subject, wherein the subject has one or more metal objects and identifies a material that forms the one or more metal objects and a radiation energy level used to generate the obtained image. The obtained radiographic image is segmented to identify boundaries of the metal object. A conditioned radiographic image is formed by replacing pixel values in the radiographic image that correspond to the one or more metal objects with compensating pixel values according to the identified material and the identified radiation energy level. The conditioned radiographic image is then displayed.

18 Claims, 8 Drawing Sheets

METAL ARTIFACTS REDUCTION FOR CONE BEAM CT

FIELD OF THE INVENTION

The invention relates generally to the field of diagnostic imaging and in particular to Cone-Beam Computed Tomography (CBCT) imaging. More specifically, the invention relates to a method for improving CBCT results by reducing metal artifacts in the reconstructed image.

BACKGROUND OF THE INVENTION

3-D volume imaging has proved to be a valuable diagnostic tool that offers significant advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) or cone beam CT technology offers considerable promise as one type of diagnostic tool for providing 3-D volume images. Cone beam CT systems capture volume data sets by using a high frame rate flat panel digital radiography (DR) detector and an x-ray source, typically affixed to a gantry that revolves about the object to be imaged, directing, from various points along its orbit around the subject, a divergent cone beam of x-rays toward the subject. The CBCT system captures projection images throughout the source-detector orbit, for example, with one 2-D projection image at every degree increment of rotation. The projections are then reconstructed into a 3D volume image using various techniques. Among the most common methods for reconstructing the 3-D volume image are filtered back projection (FBP) approaches.

Although 3-D images of diagnostic quality can be generated using CBCT systems and technology, a number of technical challenges remain. Highly dense objects, such as metallic implants, appliances, surgical clips and staples, dental fillings, and the like can cause various image artifacts that can obscure useful information about the imaged tissue. Dense objects, having a high atomic number, attenuate X-rays in the diagnostic energy range much more strongly than do soft tissue or bone features, so that far fewer photons reach the imaging detector through these objects. For 3-D imaging, the image artifacts that can be generated by metallic and other highly dense objects include dark and bright streaks that spread across the entire reconstructed image. Such artifacts can be due to physical effects such as high quantum noise, radiation scatter, beam hardening, and non-linear amplification in FBP reconstruction. These artifacts can reduce image quality by masking soft tissue structures, not only in the immediate vicinity of the dense object, but also throughout the entire image. At worst, this can falsify CT values and even make it difficult or impossible to use the reconstructed image effectively in assessing patient condition or to properly plan radiation therapy or other suitable treatments.

A number of approaches have been tried for metal artifacts reduction (MAR), with varying success and some shortcomings. Three basic types of approaches have been used:

1. Interpolation-based FBP reconstruction approach. This approach operates in the projection domain, where the metal shadow is identified and obscured values interpolated using nonmetal contaminated neighbors. For some types of imaging, with a single metal object within a relatively homogeneous volume, this method works acceptably. However, in more complex heterogeneous tissue, particularly where there are multiple metal objects in a heterogeneous volume, the interpolation-based algorithm can make unrealistic assumptions about the volume segment that lies in the shadow of the object (s), leading to prominent errors in the reconstructed images. Theoretically, it is known in the 3-D imaging arts that any interpolation-based repair scheme of the Radon space is based on a weak underlying model. Hence, it cannot be expected that the estimated projection data will perfectly fit the projection data measured without metal objects.

2. Iterative reconstruction approach. Generally improved over the performance of interpolation-based FBP (1), the iterative reconstruction approach is also more successful for severely distorted images. Iterative reconstruction uses some prior knowledge of the image physics, noise properties, and imaging geometry of the system. For this method, it is necessary to have information about the shape and location and, possibly, the attenuation coefficients of the metal objects in the reconstruction image domain. Typically, a constrained optimization approach is applied, which can be very sensitive to system configurations and to the quality of the projection data. These requirements are easily met for computer simulation or phantom imaging, and have been experimentally tested by researchers; however, iterative reconstruction may be impractical for clinical use, where volume geometries are considerably more complex than those used in simulation. Furthermore, iterative reconstruction methods are computationally much more intensive than FBP, making these methods less practical for clinical use in commercial CT scanning apparatus.

3. Quasi-iterative based FBP approach. The quasi-iterative based FBP approach performs clustering in the reconstruction domain after the initial 3-D image reconstruction, without any metal correction or with metal correction introduced in approach 1 (above). The voxel elements of the reconstructed volume are classified into several tissues, such as soft tissue, bone, air, etc., with each voxel assigned a value corresponding to one of these tissue types. This method then forward projects the classified reconstruction volume onto each metal-affected detector element and subsequently a final reconstruction of the thus modified raw data to obtain the metal artifacts reduced volume. This method outperforms the interpolation-based FBP approach. The most prominent feature of this method is suppression of secondary artifacts caused by the interpolation scheme. However, one drawback of this method is that it fails whenever the interpolation based approach (1) fails. Moreover, quasi-iterative processing cannot handle the case where the object size exceeds the field of view, since additional artifacts caused by the forward projection are introduced in the corrected images.

It is recognized that metal artifacts reduction can be a challenging task, particularly for more complex implant geometries. In spite of some progress that has been made using exemplary approaches (1)-(3) given previously, there is still considerable room for improvement and a need for a method of metal artifacts reduction that offers improved performance and computational efficiency.

SUMMARY OF THE INVENTION

An aspect of this application is to advance the art of volume imaging.

Another aspect of this application to address in whole or in part, at least the foregoing and other deficiencies in the related art.

It is another aspect of this application to provide in whole or in part, at least the advantages described herein.

It is another aspect of this application to provide methods and/or apparatus embodiments to reduce metal artifacts in CBCT volume images. Processing can be provided in the projection domain to improve the overall efficiency of the process and/or reduce computational demands.

These aspects are given only by way of illustrative example, and such aspects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for suppressing metal artifacts in a radiographic image, the method executed at least in part on a computer and comprising obtaining at least one two-dimensional radiographic image of a subject, wherein the subject has one or more metal objects; identifying a material that forms the one or more metal objects and a radiation energy level used to generate the obtained image; segmenting the obtained radiographic image to identify boundaries of the metal object; forming a conditioned radiographic image by replacing pixel values in the radiographic image that correspond to the one or more metal objects with compensating pixel values according to the identified material and the identified radiation energy level; and displaying the conditioned radiographic image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of preferred embodiments of the invention, reference being made to the drawings in which the same reference numerals identify the same elements of structure in each of the several figures.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

In the context of the present disclosure, the term "volume image" is synonymous with the terms "3-dimensional image" or "3-D image". Embodiments of the present invention are particularly well suited for suppressing the types of metal artifacts that occur in 3-D volume images, including cone-beam computed tomography (CBCT) as well as fan-beam CT images. However, it should be noted that the artifacts reduction approach described herein is also applicable for 2-D radiographic images, as described in more detail subsequently.

For the image processing steps described herein, the terms "pixels" for picture image data elements, conventionally used with respect 2-D imaging and image display, and "voxels" for volume image data elements, often used with respect to 3-D imaging, can be used interchangeably. It should be noted that the 3-D volume image is itself synthesized from image data obtained as pixels on a 2-D sensor array and displays as a 2-D image from some angle of view. Thus, 2-D image processing and image analysis techniques can be applied to the 3-D volume image data. In the description that follows, techniques described as operating upon pixels may alternately be described as operating upon the 3-D voxel data that is stored and represented in the form of 2-D pixel data for display. In the same way, techniques that operate upon voxel data can also be described as operating upon pixels.

In the context of the present disclosure, high-density objects that cause what is commonly known as metal artifacts in the volume image are termed "metal" objects. This includes objects formed from materials having a relatively high mass attenuation coefficient. The mass attenuation coefficient for a material is not a fixed value, but varies dependent, in part, on the photon energy level. An exemplary metal object of titanium, for example, has a mass attenuation coefficient of 4.972 $cm^2/g$ at 30 keV and a mass attenuation coefficient of 0.4052 $cm^2/g$ at 80 keV. Any object having attenuation at or near that of titanium or higher can be considered to be a metal object. It should be noted, for example, that objects formed from some types of highly dense composite materials can have a similar effect on image quality. The methods of the present invention address the type of artifact generated by such an object, of whatever material type or other composition. Materials commonly used and known to cause at least some type of "metal artifact" in radiographs and volume images include metals such as iron, cobalt, chromium, titanium, tantalum, and alloys including cobalt chromium alloys, for example, as well as some ceramic compositions and various composite materials such as high density composite plastics.

CBCT imaging apparatus and the imaging algorithms used to obtain 3-D volume images using such systems are well known in the diagnostic imaging art and are, therefore, not described in detail in the present application. Some exemplary algorithms and approaches for forming 3-D volume images from the source 2-D images, projection images that are obtained in operation of the CBCT imaging apparatus can be found, for example, in the teachings of U.S. Pat. No. 5,999,587 entitled "Method of and System for Cone-Beam Tomography Reconstruction" to Ning et al. and of U.S. Pat.

No. 5,270,926 entitled "Method and Apparatus for Reconstructing a Three-Dimensional Computerized Tomography (CT) Image of an Object from Incomplete Cone Beam Data" to Tam.

In typical applications, a computer or other type of dedicated logic processor for obtaining, processing, and storing image data is part of the CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice method embodiments according to the application.

Figure 1:
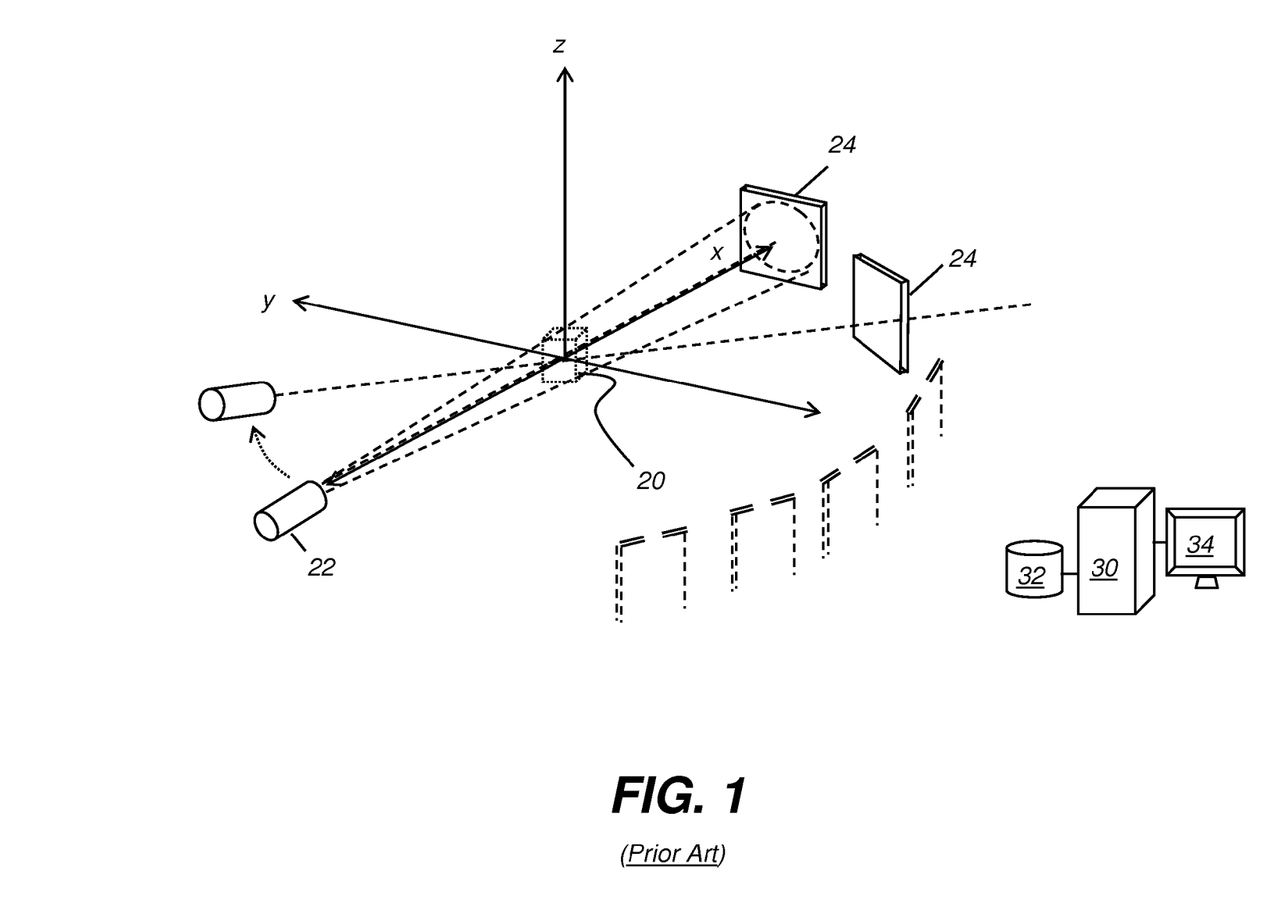
FIG. 1 is a block diagram schematic that shows how projection images are obtained.

In order to more fully understand exemplary method embodiments of the application and problems addressed, it is instructive to review principles and terminology used for CBCT image capture and reconstruction. Referring to the perspective view of FIG. 1, there is shown, in schematic form and using enlarged distances for clarity of description, the activity of a conventional CBCT imaging apparatus for obtaining the individual 2-D images that are used to form a 3-D volume image. A cone-beam radiation source 22 directs a cone of radiation toward a subject 20, such as a patient or other subject. A sequence of images is obtained in rapid succession at varying angles about the subject, such as one image at each 1-degree angle increment in a 200-degree orbit. A DR detector 24 is moved to different imaging positions about subject 20 in concert with corresponding movement of radiation source 22. FIG. 1 shows a representative sampling of DR detector 24 positions to illustrate how these images are obtained relative to the position of subject 20. Once the needed 2-D projection images are captured in this sequence, a suitable imaging algorithm, such as filtered back projection (FBP) or other conventional technique, is used for generating the 3-D volume image. Image acquisition and program execution are performed by a computer 30 or by a networked group of computers 30 that are in image data communication with DR detectors 24. Image processing and storage is performed using a computer-accessible memory 32. The 3-D volume image can be presented on a display 34.

FBP is a discrete implementation of an analytic model that assumes that CT transmission measurements are linear functions of the attenuation line integrals along the corresponding primary photon trajectories through the subject and are noiseless. When scanning subjects comprised of only anatomically native materials under normal conditions, relatively simple corrections to the raw projection data are sufficient to assure that these assumptions (e.g., linear relationship) are at least approximately true. This treatment allows FBP images that are free of visually observable artifacts. However, in regions shadowed by highly dense, attenuating objects such as metal, there is a dramatic increase in noise and nonlinear detector response, which can be caused by scatter and beam hardening. This can give rise to pronounced streaking artifacts. Mismatches between the simplified FBP model of detector response and the physical process of signal acquisition when metal objects are in the scanning field of view are the main source of those metal artifacts. An accurate physical model of the CT signal acquisition process is useful to mitigate the metal artifacts based on FBP reconstruction.

Figure 2:
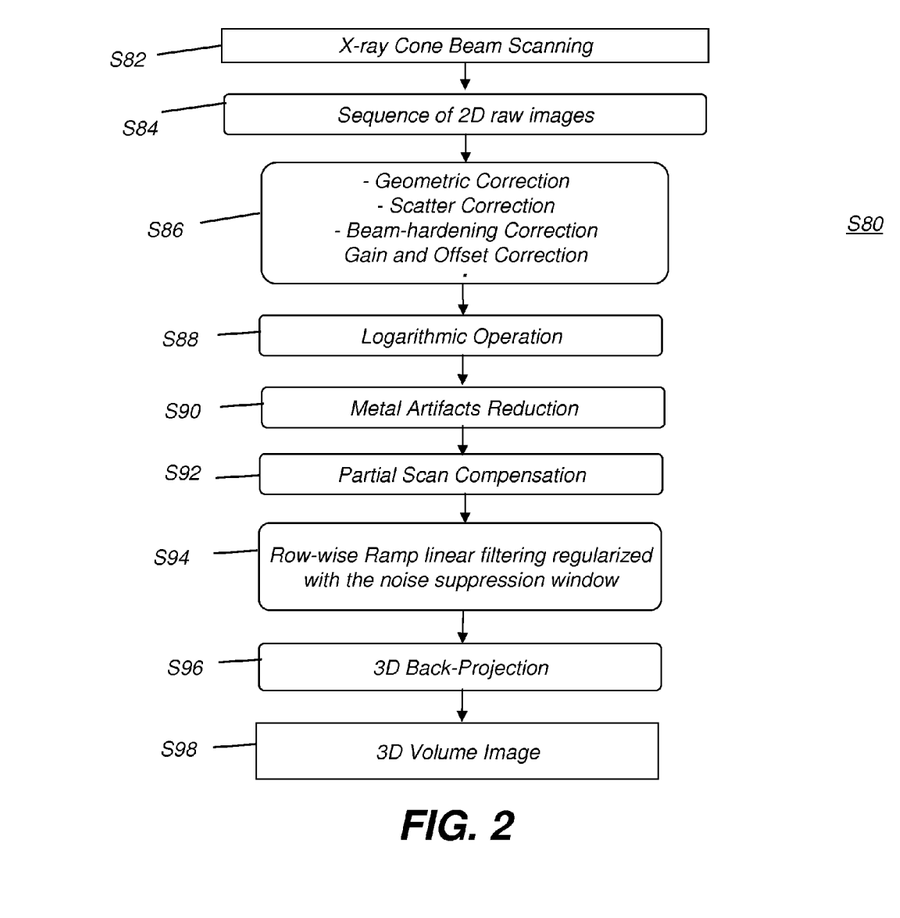
FIG. 2 is a logic flow diagram that shows the use of metal artifacts reduction in volume image processing workflow.

The logic flow diagram of FIG. 2 shows an image processing sequence S80 for CBCT reconstruction that includes processing to suppress metal artifacts. A scanning step S82 directs cone beam exposure toward the subject, enabling collection of a sequence of 2-D raw data images for projection over a range of angles in an image data acquisition step S84. An image correction step S86 then performs standard processing of the projection images for geometric correction, scatter correction, gain and offset, and beam hardening. A logarithmic operation step S88 obtains the line integral data that is used for conventional reconstruction methods, such as the FDK method well-known to those skilled in the volume image reconstruction arts. A metal artifacts reduction step S90 is then used where the obtained images include metal or other highly dense objects.

An optional partial scan compensation step S92 is then executed when it is necessary to correct for constrained scan data or image truncation and related problems that relate to positioning the detector about the imaged subject throughout the scan orbit. A ramp filtering step S94 follows, providing row-wise linear filtering that is regularized with the noise suppression window in conventional processing. A back projection step S96 is then executed and an image formation step S98 reconstructs the 3-D volume image using one or more of the non-truncation corrected images. FDK processing generally encompasses the procedures of steps S94 and S96. The reconstructed 3-D image can then be stored in a computer-accessible memory and displayed.

Figure 3:
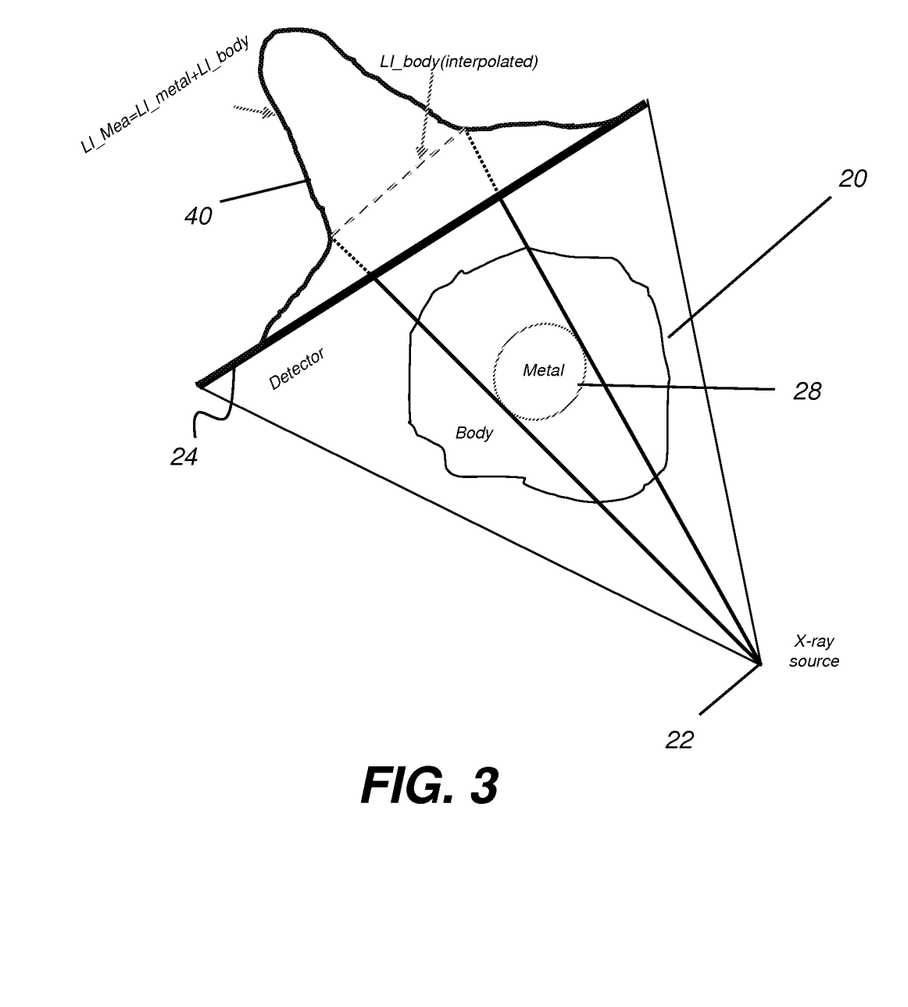
FIG. 3 is a top view schematic diagram showing the effect of a metal object when a projection image is formed.

The schematic drawing of FIG. 3 shows, from a top view, how the line integrals for each portion of the projected cone beam combine to provide image data in each projection image. A graph 40 shows values for each line integral at the projection angle. As can be seen from this image, line integrals for rays that travel through a metal object 28 are markedly higher in value than those that travel through or alongside subject 20. Interpolation, indicated by the dashed line across points on graph 40, smoothes out the line integral data and provides at least an approximation of the actual data without metal object 28. Where the surrounding tissue of subject 20 is homogeneous or very uniform, interpolation can have acceptable accuracy, and has been used with some success in such cases, as noted previously in the background section. However, some amount of information is lost in interpolation.

Figure 4:
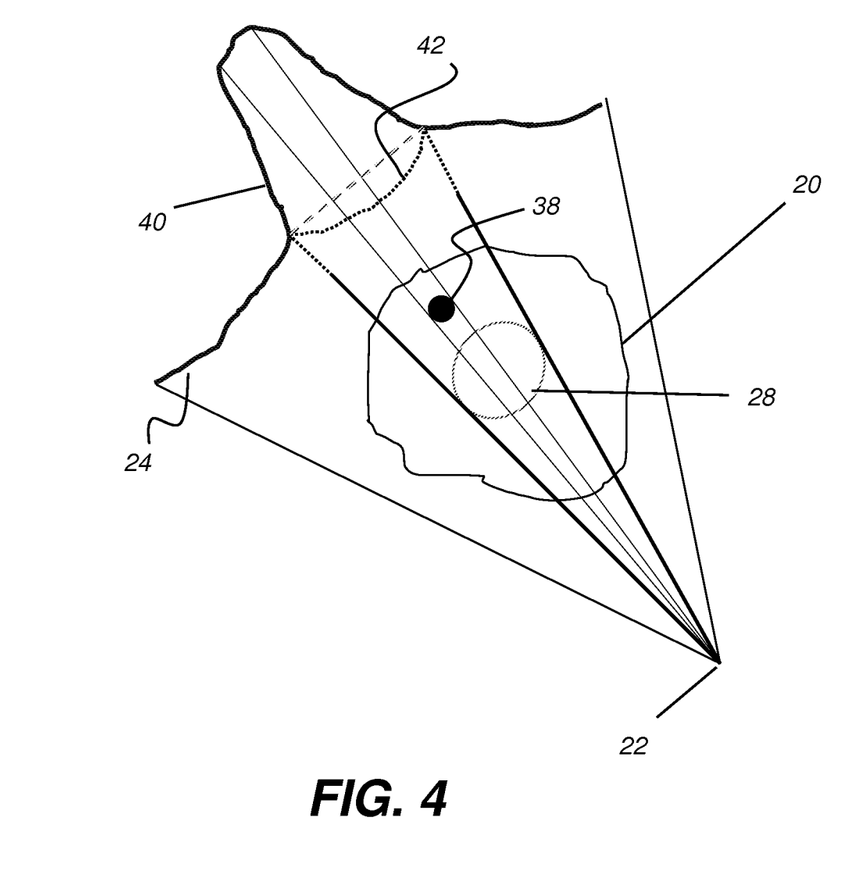
FIG. 4 is a top view schematic diagram showing a projection through a metal object and with an air hole.

The schematic drawing of FIG. 4 shows a situation for which interpolation results are particularly poor. An air hole 38 lies in the shadow area of metal object 28. Boundary portions of air hole 38 will be lost in the reconstruction image if interpolation is used. Some streak artifacts may be suppressed, but this is at the expense of unpredictable artifacts in the metal shadow area, which may also affect anatomy reconstruction.

Conventional methods for suppressing metal artifacts, as described previously in the background, prove to be unsatisfactory in many instances. Embodiments of the present invention address problems of reducing metal artifacts while attempting to retain a larger portion of the image data than is available using interpolation as shown in FIG. 3. To do this, embodiments of the present invention, using previously obtained information about the dense material that forms the object and about the energy level of the radiation used for imaging, process the projection image to replace image elements that correspond to the dense object with surrogate data such as surrogate data image elements that have an adjusted, compensating density. As a result, at least some portion of data from the surrounding tissue, even though it is in the shadow portion of the metal object, is retained in the projection image.

The compensating density for substitution values is predetermined, based on at least the dense material (e.g., atomic number) from which the object is formed and the energy level that is used. From a sampling of phantom or other images, image information is obtained that helps to profile how completely a given material blocks radiation at a given energy level. By combining this information for a material with the projection image of a subject that includes an object formed from the material, a difference image can be obtained that includes information about the surrounding tissue. By way of example, FIG. 4 shows a resealed portion 42 of graph 40 that shows the inverted data that results from this processing.

In order to suppress metal artifact effects, two variables are of interest: the material used for the implant, that is, metal or other dense material; and the X-ray tube energy, in terms of kVp setting. Given this information, new values are calculated as follows:

$$\text{pro\_seg} = (-1 * (\text{pro\_}m\text{\_seg} - \text{inp\_}m\text{\_seg}) / \beta(\gamma_m, \gamma_{kVp})) + \text{inp\_}m\text{\_seg}$$

Wherein:
pro_seg: newly generated metal shadow data;
pro_m_seg: original metal shadow data;
inp_m_seg: interpolated data in the metal shadow;
$\beta(m, kVp)$: scaling function of the material used for implant and tube kVp.

The process is conducted in row-wise fashion. In the formula given above, subtraction of interpolated data from the original metal shadow data (pro_m_seg−inp_m_seg) provides normalization that accounts for the thickness of the metal object at that location. The function $\beta(\gamma_m, \gamma_{kVp})$ is used as a divisor for resealing the normalized result. Function $\beta(\gamma_m, \gamma_{kVp})$ can be empirically determined and relates to the type of metal object $\gamma_m$ that would otherwise cause artifacts and the radiation energy at the given tube kVp setting, $\gamma_{kVp}$. Parameters $\gamma_m$ and $\gamma_{kVp}$ can be determined experimentally through either prototype or bench-top system scanning of the implants made of different materials and under different tube kVp settings.

Applying this processing to image data elements in the path of rays extending through the metal object has been found to provide a more accurate view of the volume data than is achieved using conventional metal artifact reduction methods. The inventors have observed the following:

(i) Significant reduction of fine streak artifacts induced by the edge-gradient at the boundaries between the metal object and surrounding tissue. This effect can be achieved by replacing image elements for the metal object with image elements having a compensating density value.

(ii) Beam hardening correction can be conducted on the original metal shadow segment prior to processing using the proposed scheme so as to make body part information more consistent with information viewed from other projection angles that do not have the metal object in the path.

(iii) For less dense implants, this scheme helps to obtain more information about nearby tissue in the shadow of the metal object.

(iv) For very dense implants, embodiments of apparatus and/or methods according to the application show a dramatic reduction in dark band artifacts.

(v) Implant material characteristics under different kVp conditions can be recorded and used for other implants and objects of the same material. In one embodiment, it should be noted that obtaining shape and size information for the metal object is unnecessary when using the processing described herein; the material itself must be identified, however.

Advantageously, embodiments of the application can process the original 2-D projection data, rather than processing the 3-D volume data. This can simplify processing and/or help to avoid problems such as potential mismatch between the surrogate data (which is forward projected from the reconstruction volume) and the surrounding originally measured data, as is a problem encountered when using the conventional quasi-iterative based FBP approach noted in the background section.

Processing Sequence

Figure 5A:
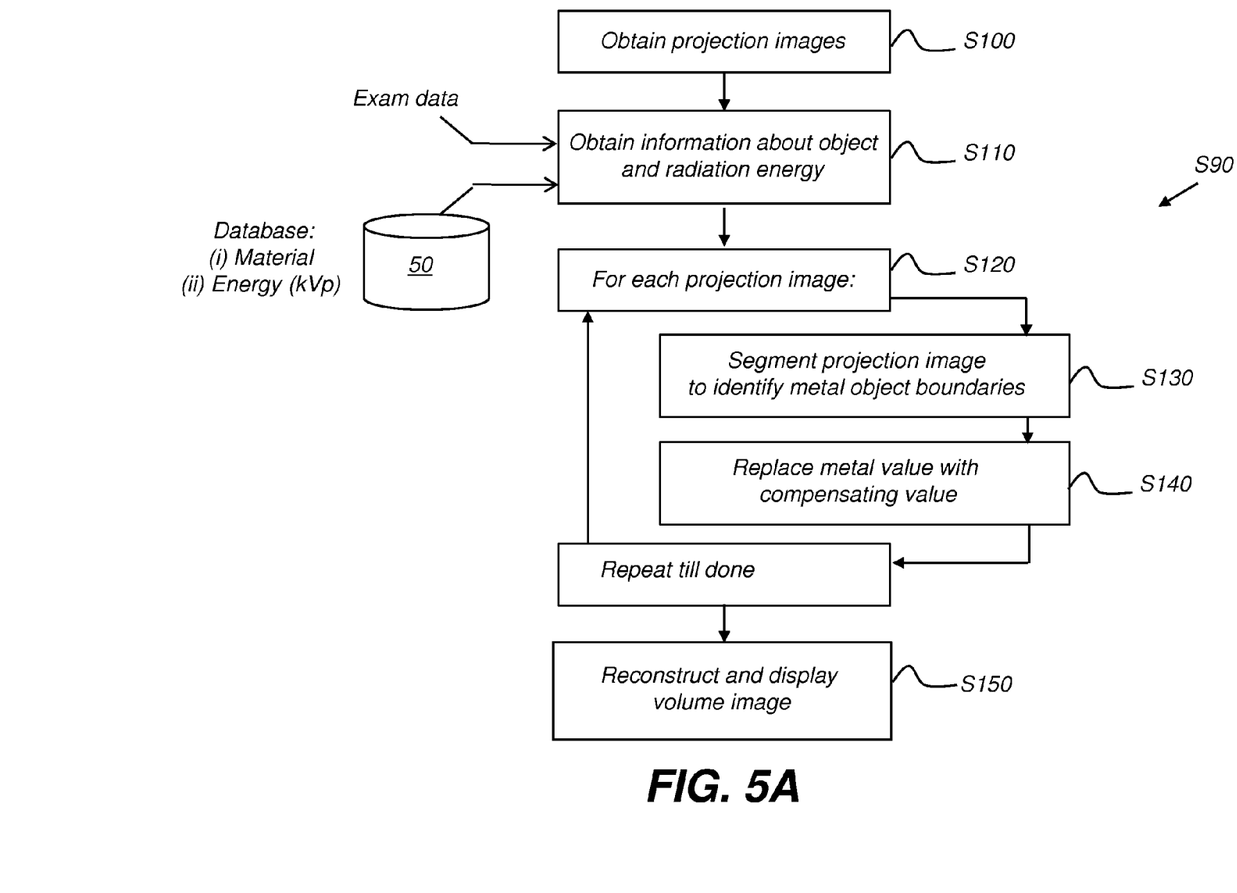
FIG. 5A is a logic flow diagram showing the sequence for metal artifacts suppression for volume imaging according to an embodiment of the present invention.

The logic flow diagram of FIG. 5A shows a sequence for generating a volume image with suppressed metal artifacts, using metal artifacts reduction step S90 as described with reference to FIG. 2, according to an embodiment of the present invention. In an obtain projections step S100, projection images, as shown in FIG. 1, are obtained at several angles about the subject. In an exam data definition step S110, information is obtained about the material that is used in the metal implant or other metal or high density material object and about the energy used, as a kVp value or expressed in terms of some other suitable energy measurement. In a looping sequence S120, each projection is processed individually, with a segmentation step S130 and a pixel replacement step S140. A reconstruction and display step S150 then uses the projections to form the corrected volume image.

FIG. 5A also shows other sources of information used for executing the process of the steps shown. In one embodiment, a database 50 has been previously generated, with surrogate values used to substitute for a variety of types of material at a range of energy (kVp) settings. Exam data for the particular volume imaging session can be obtained from the user interface. The user interface, for example, may prompt the user to enter information related to the type of material used for metal objects in the corresponding image. Alternately, information about the material used for the metal objects and the energy level used can be stored along with the image data, such as in data stored in a header file, for example. In one embodiment, information about a first energy level (e.g., kVp setting) for a given material can be determined from additional energy level(s) for the given material (e.g., interpolation), which can increase the range of energy level settings available to a user.

It should also be noted that an alternate embodiment of the present invention performs metal artifacts reduction on 2-D radiographic images, rather than for volume images as described with reference to FIG. 5A, but using a similar processing sequence. Referring to the logic flow diagram of FIG. 5B, an obtain image step S200 acquires radiographic image data that includes a metal object. In an exam data definition step S210, information is obtained about the material that is used in the metal implant or other metal or high density material object and about the energy used, as kVp value or using some other suitable energy measurement. A segmentation step S220 segments the image to identify boundaries of the metal object(s) contained in the image. A pixel replacement step S230 then forms a conditioned image by replacing each metal pixel value with a suitable compensating value. A display step S250 then displays the conditioned image resulting from this metal artifacts reduction processing.

Figure 5B:
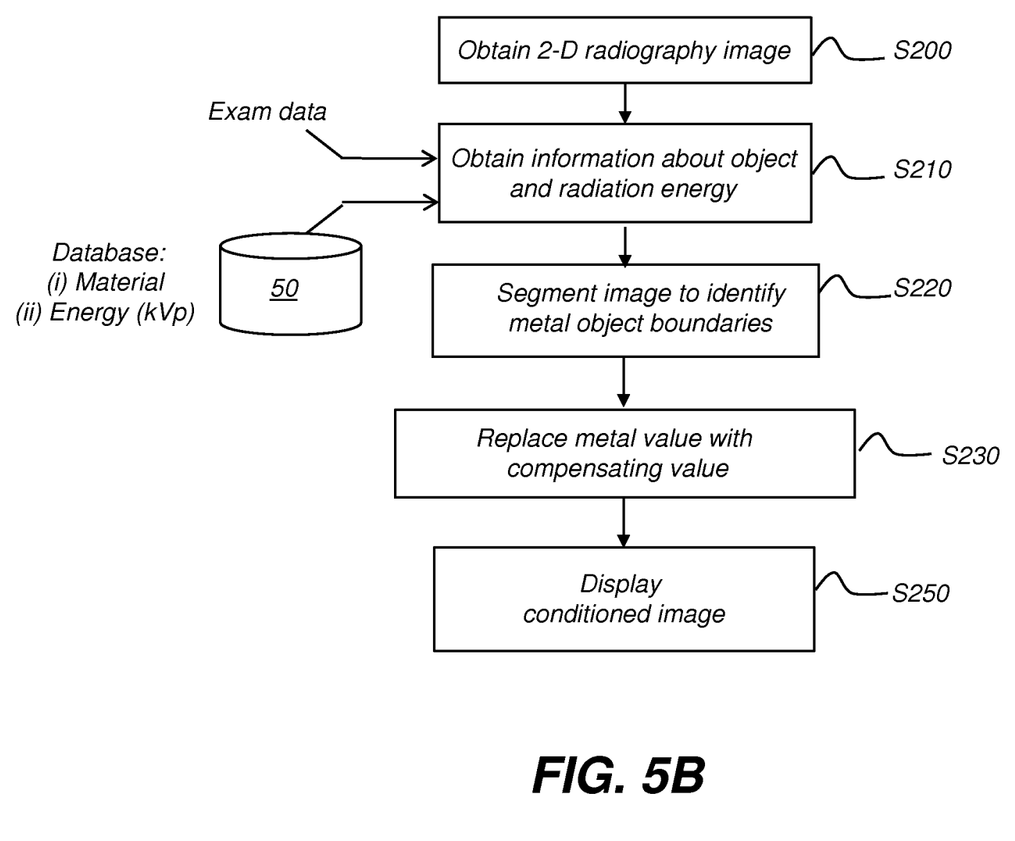
FIG. 5B is a logic flow diagram showing the sequence for metal artifacts suppression for 2-D radiographic imaging according to an embodiment of the present invention.
Figure 6:
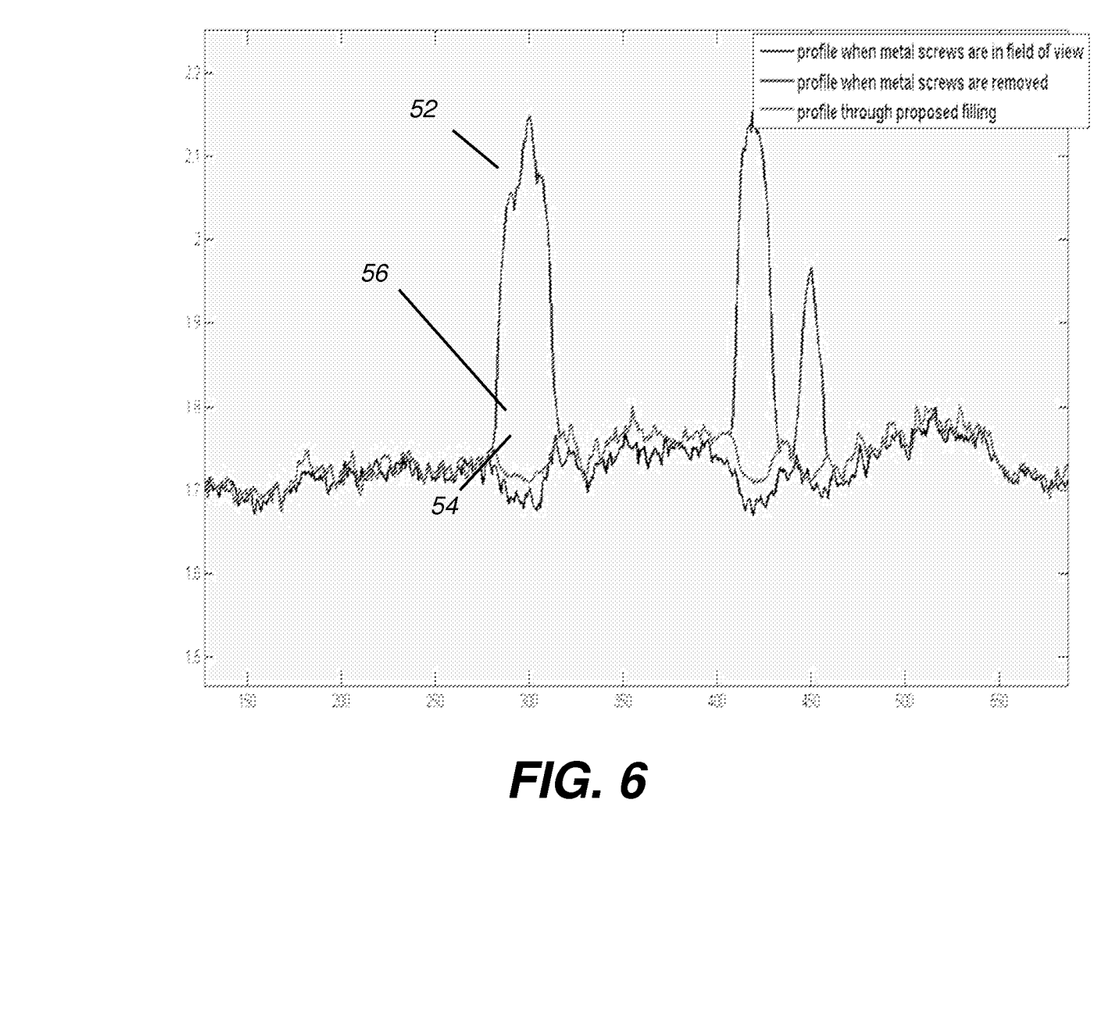
FIG. 6 is a graph that shows comparative results when using an embodiment of the present invention to suppress metal artifacts.

Image processing using the sequence of FIG. 5A or 5B has been shown to provide a more accurate 3-D volume image reconstruction than is provided using more conventional metal artifacts suppression routines. By way of example, FIG. 6 shows a profile comparison for a projection image of a phantom having three metal objects in series, imaged with and without the metal objects. Each metal artifact causes the peak effect shown in this graph along a curve 52. A curve 54 shows data along the same position with the metal objects removed (e.g., replaced by air). A curve 56 shows the results of metal artifacts reduction using the processing sequence of the present invention. Notably, curve 56 closely tracks curve 54 and compensates for the peak effects shown, due to metal objects, that result in curve 52.

Figure 7A:
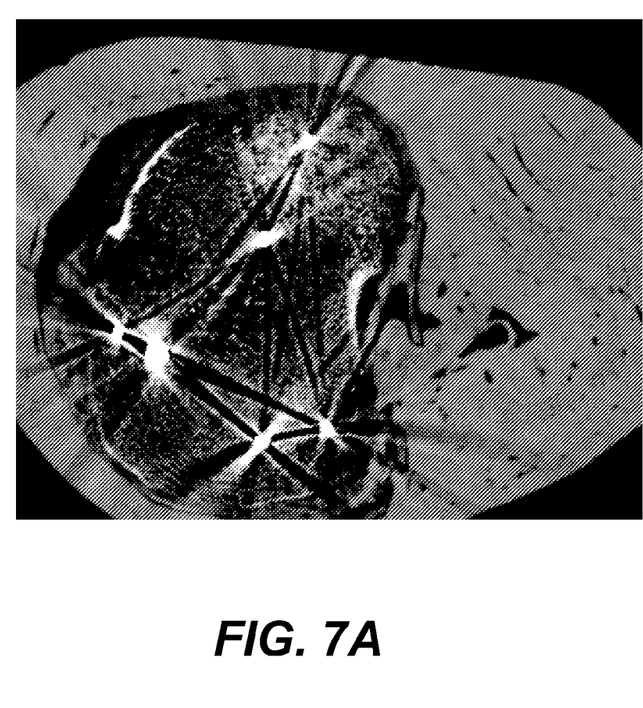
FIG. 7A is a view of a projection image having metal artifacts.
Figure 7B:
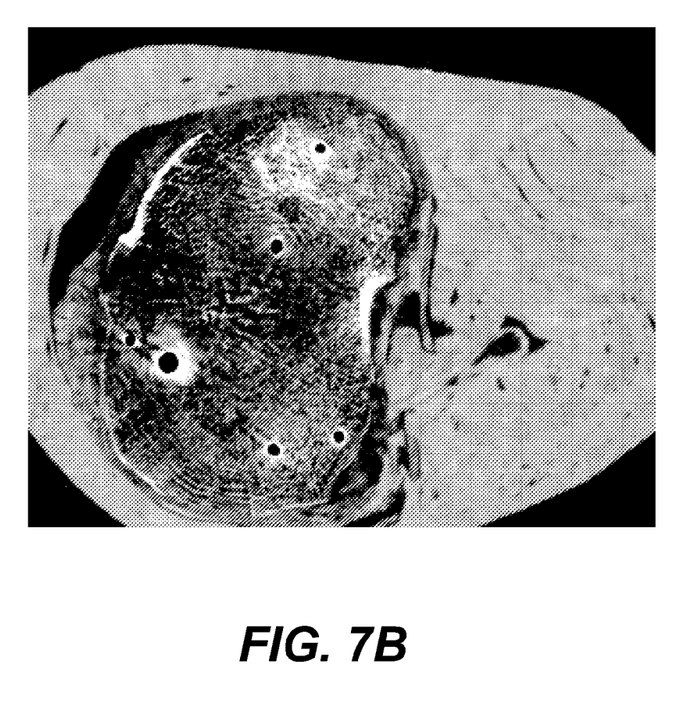
FIG. 7B is a view of the projection image of FIG. 7A, processed to reduce or remove the metal objects and their corresponding artifacts according to an embodiment of the present invention.

By way of example, FIG. 7A shows a reconstructed image of an anatomical feature having metal objects. The artifacts due to the metal objects are clearly visible and obscure the visibility of nearby features as well. FIG. 7B shows results after processing for metal artifacts reduction, as described herein. Metal artifacts are reduced or removed and nearby features are less obstructed or unobstructed. Metal object locations appear as dark areas or "holes", as shown.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, such as database 50 described with reference to FIG. 5A, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A method for suppressing metal artifacts in a radiographic image, the method executed at least in part on a computer, the method comprising:
   obtaining at least one two-dimensional radiographic image of a subject generated at a radiation energy level, wherein the subject has one or more metal objects;
   identifying both a type of dense material that forms the one or more metal objects and the radiation energy level used to generate the obtained image;
   segmenting the obtained radiographic image to identify boundaries of the metal object;
   forming a conditioned radiographic image by replacing pixel values in the radiographic image that correspond to the one or more metal objects with compensating pixel values based on both the identified type of dense material and the identified radiation energy level; and
   displaying, storing, or transmitting the conditioned radiographic image.

2. The method of claim 1 wherein replacing the pixel values comprises subtracting interpolation values from original data values between the identified boundaries of the metal object and scaling and inverting the result to determine metal artifact compensation data.

3. The method of claim 2 further comprising adding the interpolation values to the metal artifact compensation data.

4. The method of claim 1 wherein identifying the type of dense material comprises obtaining information from an image file header.

5. The method of claim 1 wherein identifying the type of dense material comprises obtaining information from an operator interface.

6. The method of claim 1 wherein the at least one two-dimensional radiographic image of the subject is a projection image from a computed tomography apparatus.

7. A method for suppressing metal artifacts in a volume image, the method executed at least in part on a computer and comprising:
- obtaining a plurality of two-dimensional x-ray projection images of a subject, wherein the subject has one or more metal objects;
- obtaining a previously provided material type of a dense material that forms the one or more metal objects and a radiation energy level used to obtain the plurality of two-dimensional x-ray projection images;
- processing each of the projection images by:
  - (i) segmenting the projection image to identify boundaries of the metal object; and
  - (ii) replacing pixel values within the identified boundaries in the projection image that correspond to the metal object with compensating pixel values that relate to the material type of the dense material and the radiation energy level used to obtain the projection image;
- reconstructing the volume image from the processed projection images; and
- displaying, storing, or transmitting the reconstructed volume image.

8. The method of claim 7 wherein obtaining the previously provided material type of a dense material comprises obtaining information from an image file header.

9. The method of claim 7 wherein obtaining the previously provided material type of a dense material comprises obtaining information from an operator interface.

10. The method of claim 7 wherein reconstructing and displaying the volume image comprises using filtered back projection.

11. The method of claim 7 wherein replacing pixel values further comprises obtaining the compensating pixel values from a computer-accessible memory.

12. The method of claim 7 further comprising displaying the processed projection images in a display device.

13. The method of claim 7 wherein the projection images are from a cone-beam computed tomography system.

14. The method of claim 7 wherein the projection images are from a fan-beam computed tomography system.

15. The method of claim 7 wherein replacing pixel values further comprises subtracting interpolated data from original two-dimensional image data.

16. The method of claim 7 comprising determining the compensating pixel values by subtracting interpolation values from original data values between the identified boundaries of the metal object and scaling and inverting the result to determine metal artifact compensation data, and adding the interpolation values to the metal artifact compensation data.

17. The method of claim 7 where the replacing pixel values comprises replacing image elements for the one or more metal objects with image elements having a compensating density value calculated using the material type of the dense material and the radiation energy level used.

18. The method of claim 1 where the identified type of dense material is identified by at least its atomic number.

* * * * *

UNITED STATES PATENT AND TRADEMARK OFFICE
CERTIFICATE OF CORRECTION

| | | |
|---|---|---|
| PATENT NO. | : 9,202,296 B2 | |
| APPLICATION NO. | : 13/234472 | |
| DATED | : December 1, 2015 | |
| INVENTOR(S) | : Dong Yang et al. | |

It is certified that error appears in the above-identified patent and that said Letters Patent is hereby corrected as shown below:

On the title page

Item 73    Replace the name of Assignee "Caresteam Health, Inc." with the name -- Carestream Health, Inc. --

Signed and Sealed this
Twenty-eighth Day of June, 2016

Michelle K. Lee
*Director of the United States Patent and Trademark Office*